United States Patent
Rusz

Patent Number: 5,546,931
Date of Patent: Aug. 20, 1996

[54] ANESTHETIC-VAPOR DELIVERY APPARATUS WITH AN AMBIENT-REFERENCED PRESSURE REGULATOR

[76] Inventor: Tibor Rusz, 1508 Tejana Mesa Place N.E., Albuquerque, N.M. 87112

[21] Appl. No.: 545,907

[22] Filed: Oct. 19, 1995

[51] Int. Cl.$^6$ ................................................ A61M 15/00
[52] U.S. Cl. .............................. 128/203.12; 128/203.14; 128/203.24; 128/203.25
[58] Field of Search ........................ 128/203.12, 203.14, 128/203.24, 203.25, 205.11

[56] References Cited

U.S. PATENT DOCUMENTS

| | | | |
|---|---|---|---|
| 4,442,856 | 4/1984 | Betz | 128/203.14 |
| 4,770,168 | 9/1988 | Rusz et al. | 128/203.12 |
| 5,146,915 | 9/1992 | Montgomery | 128/203.12 |
| 5,168,866 | 12/1992 | Montgomery | 128/203.12 |
| 5,197,462 | 3/1993 | Falb et al. | 128/203.14 |
| 5,390,665 | 2/1995 | Leach | 128/203.12 |
| 5,411,019 | 5/1995 | Smith | 128/203.14 |

*Primary Examiner*—Aaron J. Lewis
*Attorney, Agent, or Firm*—Arthur K. Hooks

[57] ABSTRACT

A carrier gas source is connected to the breathing system of a patient by a carrier-gas conduit. A positive displacement gas pump has an outlet connected to a distal port in the carrier-gas conduit. A pump gas-supply conduit, includes a vaporizer chamber and an ambient-referenced pressure regulator which has an output orifice connected indirectly to the positive displacement pump inlet. In one kind of anesthetic-vapor delivery apparatus, for use with high boiling anesthetic agents, the pump gas-supply conduit has an input end connected to a proximal port in the carrier-gas conduit. In another kind of anesthetic-vapor delivery apparatus, for use with lower temperature anesthetic agents there is no proximal port. In both kinds of anesthetic-vapor delivery apparatus, the ambient-referenced regulator controls the pressure at the pump inlet to a narrow range of pressures just below ambient atmospheric pressure. A microprocessor may control the speed of the positive displacement pump for delivery of anesthetic at a chosen and accurately controlled rate. These anesthetic-vapor delivery apparatuses hold the anesthetic-vapor pressure at the inlet of the positive displacement pump to just below the ambient pressure in which the apparatus is being employed, and consequently hold constant the vapor pressure of anesthetic agent being delivered to the patient regardless of the ambient pressure and in spite of variations in the carrier gas pressure attributable to the patient's breathing system.

12 Claims, 4 Drawing Sheets

ANESTHETIC-VAPOR DELIVERY APPARATUS WITH AN AMBIENT-REFERENCED PRESSURE REGULATOR

BACKGROUND

This invention relates to an anesthetic-vapor delivery apparatus for introducing anesthetic vapor into the breathing system of a patient undergoing surgery, and more particularly pertains to such an anesthetic-vapor delivery apparatus having an ambient-referenced pressure regulator toward more accurately controlling the rate of anesthetic agent delivery to the patent at any ambient atmospheric pressure.

Anesthetic-vapor delivery apparatuses of the prior art employ a source of carrier gas, typically a mixture of oxygen and nitrous oxide, connected via a carrier gas conduit to the patient's breathing system. A vaporizer chamber is provided for holding a liquid anesthetic agent in one portion thereof and in another portion for holding the evaporated anesthetic vapor. A vaporizer inlet port is typically connected to a proximal port in the carrier-gas conduit, and a vaporizer outlet port is connected to a distal port in the carrier-gas conduit so that a portion of the carrier-gas flowing from the source to the carrier-gas conduit is diverted into the vaporizer chamber where it mixes with the anesthetic vapor. This mixture exits the vaporizer chamber and re-enters through a distal port in the carrier-gas conduit to mix with the main stream of carrier gas. This last mixture of carrier gas and anesthetic vapor is delivered to the patient's breathing system.

The concentration of anesthetic in this mixture varies as the pressure at the patient's breathing system varies, because the breathing system pressure variations are reflected at the inlet port of the vaporizer chamber and thus in this entire parallel path including in the vaporizer chamber itself. The breathing system pressure that is reflected to the carrier-gas conduit may range from ambient to 2 p.s.i. above ambient (0 to 103 cm $H_2O$ relative to ambient).

This problem has been ameliorated by adding a motor-driven positive displacement pump in the connection between the vaporizer outlet port and the distal port in the carrier-gas conduit, as is described in my U.S. Pat No. 4,770,168 issued Sep. 13, 1988. The positive displacement pump prevents changes in the breathing system from passing through the pipe connecting the distal port of the carrier-gas conduit to the vaporizer chamber.

However, pressure variations, though reduced, are still manifested in the vaporizer chamber and at the inlet of the pump, having been passed to the vaporizer chamber through the proximal conduit port.

The breathing-system variations in pressure that are reflected in the vaporizer chamber have the detrimental effect that the anesthetic-laden gas, with a given anesthetic concentration, is drawn into the positive displacement pump, and during a moment of pressure increase the rate of anesthetic delivery rises and during a moment of pressure decrease the rate of anesthetic delivery drops. Consequently the rate of anesthetic delivery is out of control to the degree that the pressure at the pump inlet varies.

It is an object of this invention to provide an anesthetic-vapor delivery apparatus in which the gas pressure at the inlet of the positive displacement pump is held at a pressure that is fixed differential pressure relative to the ambient pressure.

It is a further object of this invention to provide such an anesthetic-vapor delivery apparatus wherein the gas pressure at the inlet of the positive displacement pump is held at the ambient atmospheric pressure.

It is yet a further object of this invention to provide such an anesthetic-vapor delivery apparatus that controls the partial pressure of the anesthetic vapor in the gas delivered to the patient.

SUMMARY OF THE INVENTION

An anesthetic-vapor delivery apparatus has a carrier-gas conduit connecting a patient's breathing system to a source of a carrier gas. A pump-gas supply conduit comprised of an anesthetic vaporizer is for holding saturated anesthetic vapor. A positive displacement pump has a pump outlet connected to a distal port in the carrier-gas conduit at which pumped anesthetic vapor may be mixed with the carrier gas prior to being delivered to the patient's breathing system. The pump inlet is connected to a vaporizer outlet port, and the pump gas-supply conduit serves as the source from which the pump sucks the anesthetic vapor.

The pump gas-supply conduit is also comprised of an ambient-referenced pressure regulator means for sensing the ambient atmospheric pressure and for maintaining the gas pressure at the pump inlet to just below the ambient atmospheric pressure. This invention recognizes the critical importance of maintaining the pressure constant at the input to the positive displacement pump in order to achieve close control of the delivery rate of an anesthetic agent to the breathing system of a patient, so that at each stroke of the pump a fixed known amount of anesthetic vapor is delivered to the patient, regardless of ambient atmospheric pressure. It is believed that this is the first anesthetic vaporizer delivery apparatus to determine and control the partial pressure of anesthetic vapor in the gas being delivered to the patient, and it is the first anesthetic vaporizer apparatus to maintain that control when operating at any altitude (any ambient pressure).

The ambient-referenced pressure regulator means is comprised of a housing with one open face, a flexible diaphragm sealed to the housing in the open face to enclose a regulator space within the housing. The housing has an output orifice from the regulator space connected directly or indirectly to the pump inlet. There is also an inlet passageway in the housing leading via an inlet orifice to the regulator space. A valve means in the inlet passageway mechanically connects to a central region of the diaphragm for opening the inlet passageway when the pressure within the regulator space lies within a narrow range of pressures just below the ambient pressure and for closing the inlet passageway when the pressure within the regulator space lies outside the narrow pressure range.

The narrow range of negative pressures is preferably about from −0.5 to −5 cm/$H_2O$ (−0.007 to −0.071 p.s.i.), and the area of the flexible membrane is more than ten times, and preferably at least 100 times, greater than the effective valving area of the valve means.

The valve means includes a funnel member mounted in the inlet passageway of the regulator which funnel member is positioned with the narrow end of the funnel member directed inwardly toward the regulator space. A plug member is positioned in the funnel member for closing the valve means, and a strut member is mechanically connects the plug member to a central region of the diaphragm. When the diaphragm flexes inwardly of the housing, and when the pressure in the regulator space falls below the least negative limit of the narrow range to cause the plug member to move outward of the funnel and to open a passageway in the funnel.

In one preferred embodiment of the invention, the inlet passageway of the ambient-referenced-pressure regulator means is connected to a proximal port in the carrier gas conduit, and the output orifice of the ambient-referenced-pressure regulator means is connected to an inlet port in another wall portion of the vaporizer chamber at the anesthetic vapor reservoir.

In a second preferred embodiment of the invention the vaporizer chamber is completely closed except for the vaporizer outlet port, and the output orifice of the ambient-referenced pressure regulator means is piped directly to the pump inlet.

Further in this second embodiment, the pump-gas supply conduit includes a low positive-fixed-pressure regulator having an inlet connected to the outlet port of the vaporizer chamber and has an outlet connected to the inlet passageway of the ambient-related pressure regulator means. The fixed-pressure regulator is for regulating the pressure at the inlet passageway of the ambient-related pressure regulator means to a positive pressure of about 1 p.s.i. (70 cm $H_2O$).

Also included is an oven means for enclosing the positive displacement pump and essentially all of the pump gas-supply conduit and for holding the pump and pump gas-supply conduit to a predetermined fixed oven temperature to prevent condensation of the anesthetic vapor therein. The oven temperature should be at least 25° C.

DESCRIPTION OF THE PREFERRED EMBODIMENTS

Figure 1:
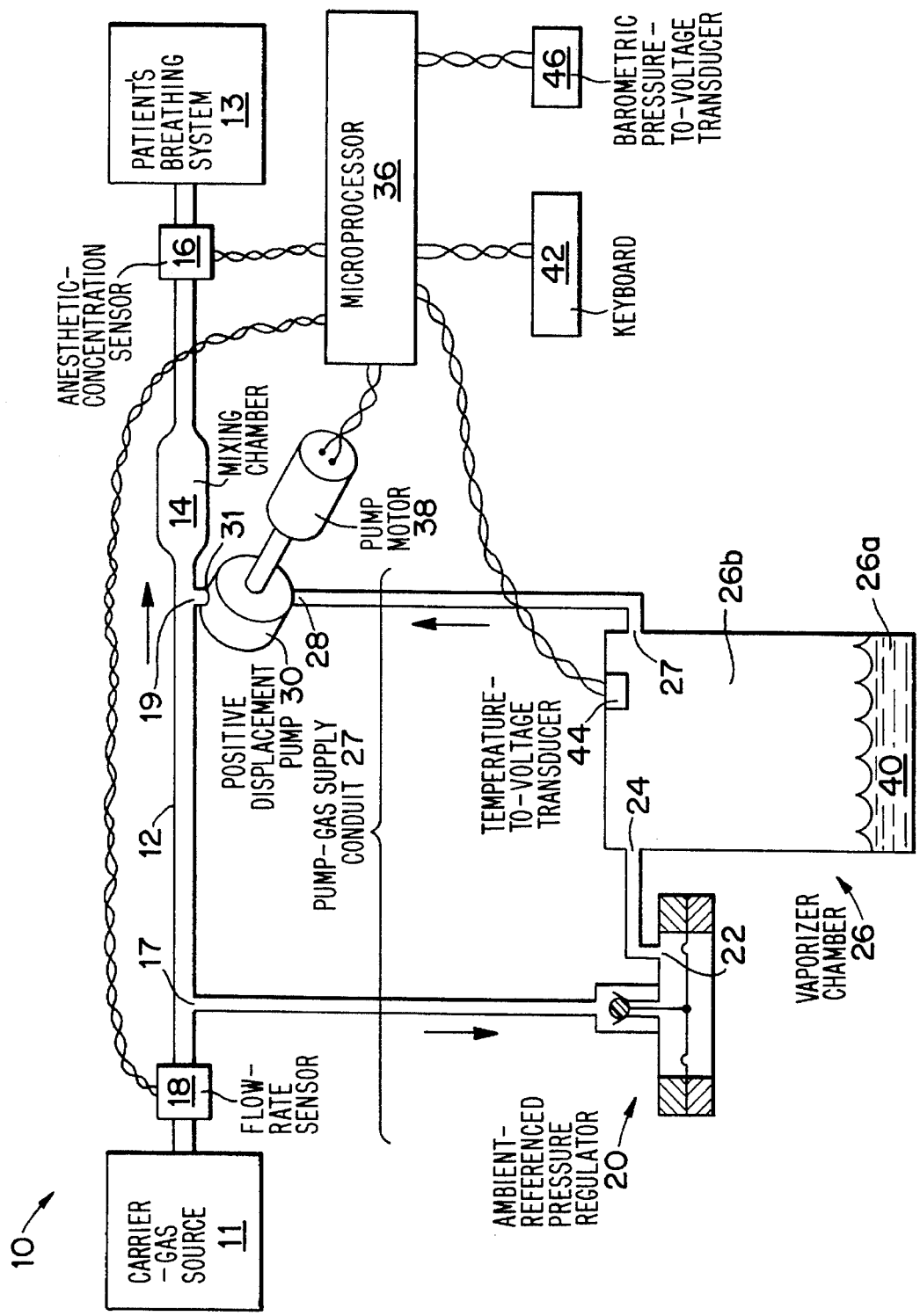
FIG. 1 shows a first embodiment of an anesthetic-vapor delivery apparatus of this invention.

The anesthetic-agent delivery system 10 in FIG. 1 has a carrier gas source 11 that delivers a carrier gas at one or more fixed flow rates. A carrier-gas conduit 12 connects the output of the carrier gas source 11 to the input of the patient's breathing system 13. The carrier-gas conduit 12 includes a mixing chamber 14 for thoroughly mixing and blending the anesthetic vapor and the carrier gases, an anesthetic concentration sensor 16, and a flow rate sensor 18. The pressure everywhere within the carrier-gas conduit 12 is approximately that of the patients' breathing system 13, i.e. varying between 0 to 2 p.s.i. above ambient (0 to 103 cm $H_2O$ relative to ambient). This and the pressures stated elsewhere herein unless otherwise noted, are positive pressures relative to the ambient atmospheric (barometric) pressure.

Figure 2:
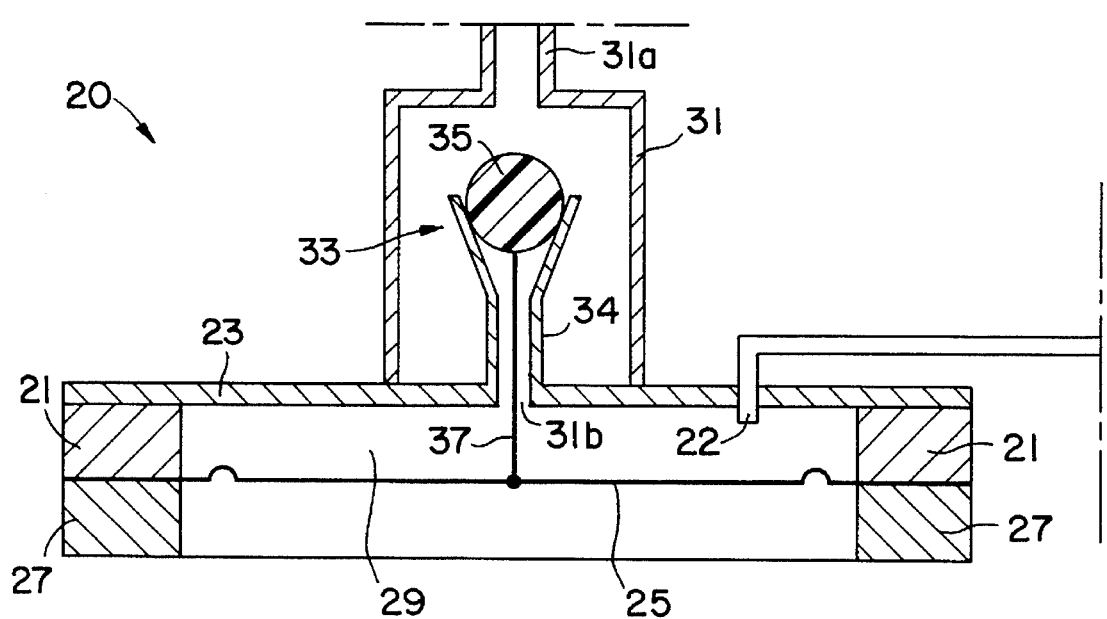
FIG. 2 shows in side sectional view an ambient pressure regulator of this invention that is employed in the anesthetic-vapor delivery apparatus of FIG. 1.
Figure 3:
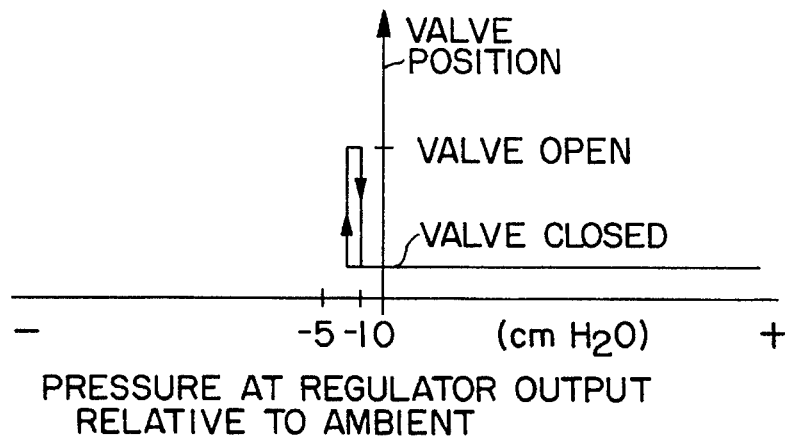

An ambient-referenced pressure regulator 20 as shown in more detail in FIG. 2, has an input connected to a proximal port 17 in the carrier-gas conduit 12, and has an output orifice 22 connected to the inlet port 24 of an anesthetic vaporizer chamber 26, as shown in FIG. 1. FIG. 3 shows an operating characteristic of regulator 20 designed to operate at about −1 cm $H_2O$.

An outlet port 27 of the vaporizer chamber 26 is connected to the inlet 28 of a positive displacement pump 30. The lower portion of vaporizer chamber 26a is for holding a liquid anesthetic agent and the upper portion 26b is for holding the anesthetic agent vapor. The inlet 28 of the positive-displacement pump 30 is connected to a distal port 19 in the carrier-gas conduit 12.

Variations amounting to 1 or 2 p.s.i. in the positive pressure of the carrier gas at port 17 in the carrier-gas conduit 12 are attributable to the patient's breathing system 13. The ambient-referenced pressure regulator 20 reduces the positive pressure to a pressure just below ambient pressure at the regulator output orifice 22. The pressure at the output of the regulator 20 is held to within a narrow range of negative pressures with respect to the ambient atmospheric pressure, e.g. −0.5 and −5 cm $H_2O$ (−0.007 to −0.071 p.s.i.).

The ambient-referenced pressure regulator 20 shown in FIG. 2 has a housing including an annular metal piece 21 with a metal plate 23 bonded to one face of the annular piece 21. This housing portion has a flexible metal diaphragm 25 bonded to the open face of annular piece 21. Another annular piece 27 of essentially the same diameter is bonded to the diaphragm 25 so as to sandwich a peripheral portion of diaphragm 25 and to provide a means for mounting the regulator 20. The housing also has an output orifice 22 in plate 23 exiting the regulator space 29 that is enclosed by the housing portion made up of annular piece 21, plate 23 and diaphragm 25. The regulator housing also has an inlet passageway 31 leading from the regulator input 31a via an inlet orifice 31b to the regulator space 29.

A valve 33 is located in the inlet passageway 31 and mechanically connects to a central region of the diaphragm 25 for opening the inlet passageway when the pressure within the regulator space lies within a narrow range of pressures just below the ambient pressure and for closing the inlet passageway when the pressure within the regulator space lies outside the narrow range.

The valve 33 has a funnel member 34 that is mounted in the inlet passageway 31 and positioned with the narrow end of the funnel member 34 connected to the regulator-space inlet orifice 31b. A plug member 35 is positioned in the funnel member 34, and a strut member 37 mechanically connects the plug member 35 to a central region of the diaphragm 25. The diaphragm 25 flexes inwardly (upward as shown) of the housing when the pressure in the regulator space 29 falls just below the ambient atmospheric pressure, e.g. −1.0 cm $H_2O$ (−0.004 p.s.i.). This causes in turn, the plug member to move outward (upward as shown) of the broad inlet end of funnel and to open a passage through the funnel member 34.

Whenever the pressure within the regulator space 29 becomes more negative than about −1 cm $H_2O$, the plug member 35 is pushed closed by the increased stream of carrier gas passing through the valve and is held there by the pressure differential from that of the carrier-gas conduit 12 (the patients' breathing system pressure averaging about 1 p.s.i.) and the slightly negative pressure in the valve space 29. The negative pressures at the regulator outlet is attributable to the sucking action of pump 30.

The limits of the narrow range of pressures at which the valve 33 remains open are determined entirely by the mechanical parameters of the regulator 20. The area of the diaphragm 25 at the rim of bonding to the piece 21 must be more than one magnitude larger, and is preferably 100 times greater, than the effective valving area of the valve 33 (where the plug member 35 seats at closing with the funnel member 34), in order to regulate the pressure at the regulator outlet to within −0.5 to −5 cm.H$_2$O.

Piece 21, plate 23 and the diaphragm 25 are preferably of stainless steel so that any back diffusion of the highly corrosive anesthetic vapors from the vaporizer chamber will not corrode them.

Figure 4:
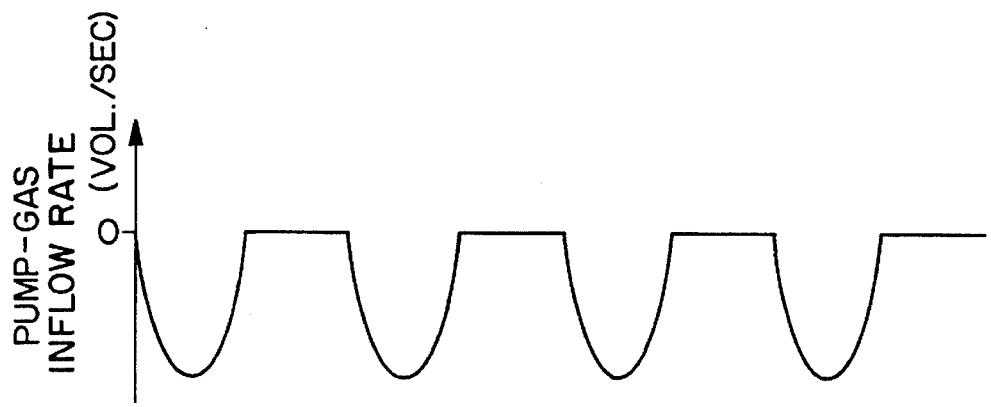
FIG. 4 shows the wave form of pump-gas inflow rate as a function of time.
Figure 5:
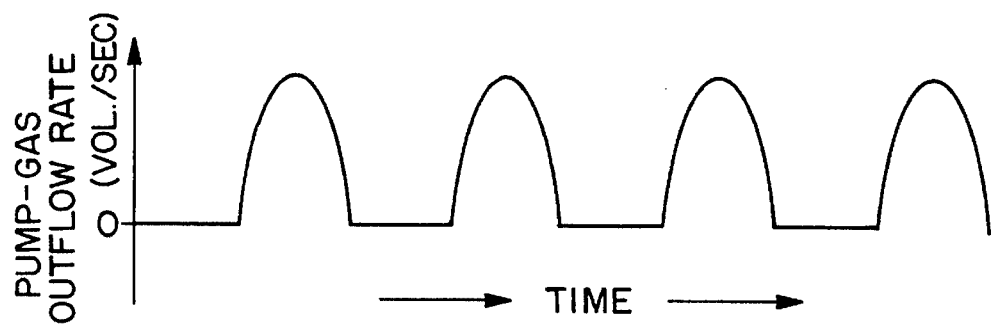
FIG. 5 shows the wave form of pump-gas outflow rate corresponding to the pump-gas inflow rate of FIG. 4 drawn to the same time scale.

The positive-displacement pump 30 periodically in each cycle sucks a fixed volume of the anesthetic-agent-laden carrier gas from the vaporizer chamber 26 as is indicated in FIG. 4, and delivers from the pump outlet 31 a volume of anesthetic-laden gas at a rate proportional to the speed at which the pump is driven, as indicated in FIG. 5.

The pressure in the vaporizer chamber 26 and the pressure at the inlet of the positive-displacement pump 30 is consequently held to just below ambient atmospheric pressure. The anesthetic vapor is maintained at saturation in the vapor reservoir 26b of the vaporizer chamber 26. The carrier gas flows through the vapor reservoir 26b which is large enough, that at the maximum anticipated carrier-gas flow rate through the vapor reservoir, saturation of the anesthetic vapor is maintained. It is convenient to think of the combination of ambient-related pressure regulator 20 and the vaporizer chamber 26 as the anesthetic-laden pump-gas supply conduit 27.

The microprocessor 36 is capable of storing the desired rate of delivery of anesthetic vapor (anesthetic-vapor molecules per minute) to the patient's breathing system 13 as instructed by the anesthesiologist via a manual input device 42 (e.g. a key board) which is electrically connected to the microprocessor 36. A temperature-to-voltage transducer 44 (e.g. a thermocouple) is for sensing the temperature in the vaporizer chamber 26. The sensor 16, or anesthetic-concentration to voltage transducer 16, and the sensor 18, or gas-flow-rate to voltage transducer 18, are each electrically connected to the microprocessor 36. The microprocessor 36 is also connected electrically to a barometric pressure-to-voltage transducer 46.

Thus, for a given pump speed, the anesthetic-laden gas flow rate is known, and for a given anesthetic agent whose characteristic vapor pressure as a function of temperature is known, the anesthetic concentration at the pump outlet is readily determined. Further when the fixed flow rate of carrier gas in conduit 12 is accounted for, the concentration of the anesthetic agent delivered to the patient's breathing system is easily determined.

A microprocessor 36 is connected electrically to the pump motor 38 which is in turn is mechanically connected to the positive-displacement pump 30 for controlling the pump speed. The pump motor 38 is preferably a stepping motor whereby the microprocessor 36 may very accurately control the pumping rate of the anesthetic-laden gas from the vaporizer chamber 26.

The vapor pressure of the liquid anesthetic agent is not a function of the pressure in the vaporizer chamber 26, but is however a function of temperature. The pressure as a function of temperature characteristic of the particular anesthetic agent 40 contained in the vaporizer chamber 26, is held in the microprocessor memory.

The microprocessor 36 is capable of calculating and controlling the speed of the positive-displacement pump 30 to achieve the desired rate of anesthetic agent delivery, accounting for the particular anesthetic agent 40, the temperature of the anesthetic vapor held in the vaporizer chamber 26, the carrier-gas flow rate, and the barometric or ambient pressure, to achieve the above-noted desired anesthetic delivery rate. In the anesthetic-vapor delivery apparatus 10 of FIG. 1, the ambient-related pressure regulator 20 holds the pressure within the anesthetic vapor reservoir 26b and at the pump inlet 28 at just below ambient atmospheric pressure. The anesthetic vapor pressure depends only upon the particular anesthetic and its temperature. Thus in the vaporizer chamber 26 wherein the anesthetic vapor is kept at saturation, the partial pressure of the anesthetic vapor is equal to the characteristic vapor pressure of the anesthetic at the temperature sensed by thermistor 44, the total gas mixture pressure is a known regulated value (regulated to just under ambient), and therefore anesthetic agent concentration is known at the pump inlet.

The beneficial results of employing the ambient-related pressure regulator 20 of this invention in the anesthetic-vapor delivery apparatus 10 is therefore twofold, improved accuracy in the control of anesthetic vapor concentration within the vaporizer chamber 26 and improved accuracy in the control of the amount of anesthetic agent being pumped at each stroke of the positive displacement pump 30.

The valve 33 in the ambient-related pressure regulator 20 also serves as a check valve to prevent diffusion of anesthetic vapor from the vaporizer chamber 26 back into the carrier-gas conduit via port 17, overcoming a problem that exists to some extent in all prior art anesthetic-vapor delivery apparatuses.

The anesthetic-vapor delivery apparatus of FIG. 1 is suitable when the anesthetic agent employed has a boiling temperature that is substantially higher than ambient temperatures, (e.g. 23° C). Some such well known high-boiling anesthetic agents are halothane U.S.P., ETHRANE and FORANE, the later two being Trademarks of Anaquest Co., Madison, Wis. These agents have boiling temperatures near 50° C.

The anesthetic-vapor delivery apparatus of FIG. 1 is not suitable for anesthetic agents having boiling temperatures near ambient such as DESFLURANE, a Trademark of Anaquest Co., Madison Wis. DESFLURANE has a boiling temperature of 22° C., and if used in the anesthetic-vapor delivery apparatus 10 would tend to condense in the pump 30, the pump inlet pipe 29 and the pump outlet pipe 31 destroying the predictability and accuracy of anesthetic concentration in the mixture flowing in the pump outlet pipe 31. This could result in extreme over dosing of the patient with anesthetic agent and even threaten the patient's life.

Figure 6:
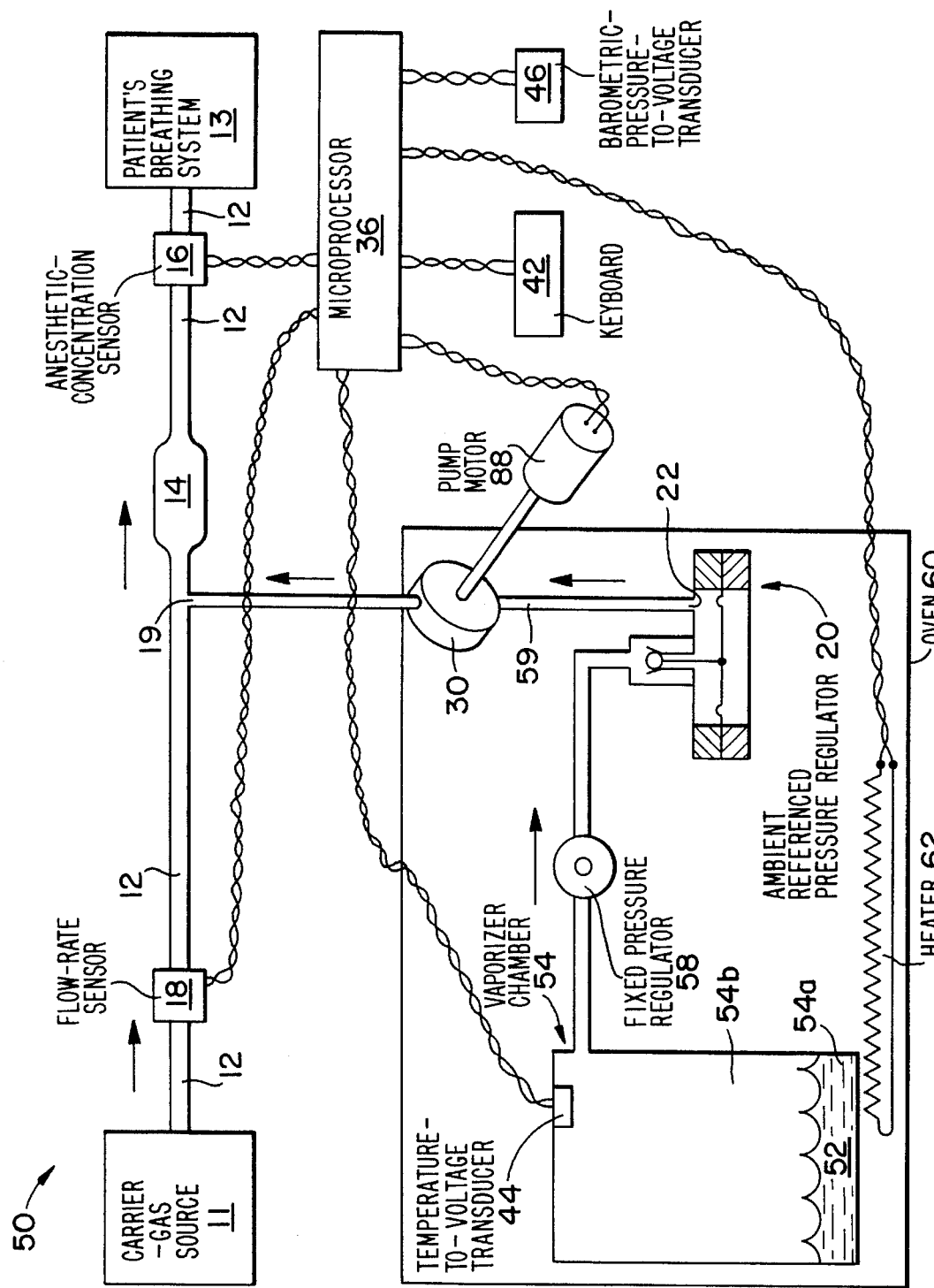
FIG. 6 shows a second embodiment of an anesthetic-vapor delivery apparatus of this invention.

The anesthetic-vapor delivery apparatus 50 shown in FIG. 6 is especially suitable for providing accurate delivery of anesthetic agents with near room temperature boiling points. The anesthetic-vapor delivery apparatus 50 relies upon the same principles for regulating the pressure at the inlet of the positive displacement pump 30 to a near ambient pressure as are manifested in the anesthetic-vapor delivery apparatus 10. The anesthetic-vapor delivery apparatus 50 of FIG. 6 uses many of the same components as are used in the anesthetic-vapor delivery apparatus 10 of FIG. 1 and those components are designated by the same numerals.

A liquid anesthetic agent 52 is loaded into the liquid-anesthetic reservoir 54a. The vaporizer chamber 54 is completely closed except for the outlet port 56. The gas in the vapor reservoir 54b of vaporizer chamber 54 is 100% anesthetic vapor and the pressure in the vapor reservoir 54b may become quite high, e.g. 30 p.s.i. The outlet port 56 from the vapor reservoir 54b is connected to the input of the ambient-referenced pressure regulator 20 via a fixed-pressure regulator 58 that holds the pressure at the input ambient-referenced pressure regulator 20 at about 1 p.s.i.

The ambient-referenced pressure regulator 20 serves exactly the same function as it did in the anesthetic-vapor delivery apparatus 10 of FIG. 1, namely, it sucks the anesthetic vapor through a pump-gas supply conduit, which in anesthetic-vapor delivery apparatus 50 comprises the vaporizer chamber 54, the fixed-pressure regulator 58, and the ambient-referenced pressure regulator 20.

All components of the pump-gas supply conduit and the pump 30 are enclosed in an oven 60. The oven 60 has a heating element 62 that is connected to the microprocessor 36, which controls and holds the temperature of all the components in the pump-gas supply conduit and the pump at a temperature above room temperature of 25° C. or higher.

In the anesthetic-vapor delivery apparatus 50 of FIG. 6, the gas in the anesthetic-vapor reservoir 54b of the vaporizer chamber 54 is entirely an anesthetic vapor, and the pressure in the vapor reservoir 54b may rise to 30 p.s.i. or higher. A fixed pressure regulator 58 reduces and regulates the pressure at the input of the ambient-referenced pressure regulator 20 to a pressure of about 1 p.s.i. The gas entering the ambient-referenced pressure regulator 20 is therefore 100% anesthetic vapor at about 1 p.s.i. The 100% anesthetic vapor at the pump inlet 28 has a pressure at just below ambient pressure, so that the amount of anesthetic vapor (number of anesthetic vapor molecules) being pumped per stroke is fixed at a known value. The pumped anesthetic vapor is then mixed with the carrier gas, also of known fixed flow rate, in the mixing chamber 14.

The major advantages of the anesthetic-vapor delivery apparatus of this invention, over those of the prior art, is higher accuracy of anesthetic-vapor delivery achieved not only at sea level but at all altitudes. This is the direct result of holding the anesthetic-vapor pressure at the inlet of the positive displacement pump to just below the ambient pressure in which the apparatus is being employed, and consequently holding constant the vapor pressure of anesthetic agent being delivered to the patient regardless of the ambient pressure and in spite of variations in the carrier gas pressure attributable to the patient's breathing system.

I claim:

1. An anesthetic-vapor delivery apparatus of the kind including a carrier-gas conduit having an inlet end into which a carrier gas may be introduced, having an outlet end to which a patient's breathing system may be connected, and having a distal port in said carrier-gas conduit; a pump-gas supply conduit comprised of an anesthetic vaporizer chamber including a liquid-anesthetic reservoir for holding a liquid anesthetic agent and an anesthetic vapor reservoir for holding evaporated anesthetic agent, said anesthetic vaporizer chamber having an outlet port in one portion of said anesthetic vapor reservoir; and a positive displacement pump having a pump outlet connected to said distal port in said carrier-gas conduit at which pumped anesthetic vapor may be mixed with a carrier gas prior to being delivered to the patient's breathing system, and having a pump inlet connected to said anesthestic vaporizer outlet port, said pump gas-supply conduit serving as a source from which said pump sucks anesthetic vapor; wherein the improvement comprises:

an ambient-referenced pressure regulator means connected in said pump gas-supply conduit for sensing ambient atmospheric pressure to the patient, and for maintaining pressure at said pump inlet to just below ambient atmospheric pressure.

2. The anesthetic-vapor delivery apparatus of claim 1 wherein said ambient-referenced pressure regulator means is comprised of a housing with one open face, a flexible diaphragm hermetically sealed to said housing in said open face to enclose a regulator space within said housing, said housing having an output orifice from said regulator space connected to said pump inlet and having an inlet passageway leading to said regulator space, and a valve means in said inlet passageway mechanically connected to a central region of said diaphragm for opening said inlet passageway when pressure within said regulator space of said ambient-referenced pressure regulator lies just below ambient pressure and for closing said inlet passageway when pressure within said regulator space lies above ambient pressure.

3. The anesthetic-vapor delivery apparatus of claim 2 wherein pressure within said regulator space is about from −0.5 to −5 cm/$H_2O$ (−0.007 to −0.075 pounds per square inch).

4. The anesthetic-vapor delivery apparatus of claim 2 wherein the area of said flexible membrane is more than an order of magnitude greater than the effective valving area of said valve means.

5. The anesthetic-vapor delivery apparatus of claim 2 wherein the area of said flexible membrane is at least 100 times greater than the effective valving area of said valve means.

6. The anesthetic-vapor delivery apparatus of claim 2 wherein said valve means is comprised of a funnel member mounted in said inlet passageway positioned with the narrow end of said funnel member directed toward said regulator space and connected to, a plug member positioned in said funnel member, and a strut member mechanically connecting said plug member to a central region of said diaphragm to cause the diaphragm to flex inwardly of said housing when the pressure in said regulator space falls just below ambient pressure to cause said plug member via said strut member to move outwardly of said funnel member to open said funnel member.

7. The anesthetic-vapor delivery apparatus of claim 2 wherein said inlet passageway of said ambient-referenced-pressure regulator means is connected to a proximal port in said carrier gas conduit, and said output orifice of said referenced-pressure regulator means is connected to an inlet port in another portion of said vaporizer chamber at said anesthetic vapor reservoir.

8. The anesthetic-vapor delivery apparatus of claim 2 wherein said anesthetic vaporizer chamber is completely closed except for said outlet port and said output orifice of said ambient-referenced pressure regulator means being piped directly to said pump inlet.

9. The anesthetic-vapor delivery apparatus of claim 8 wherein said pump-gas supply conduit additionally comprises a low positive-fixed-pressure regulator having an inlet connected to said outlet port of said anesthetic vaporizer chamber and having an outlet connected to said inlet passageway of said ambient-referenced pressure regulator means.

10. The anesthetic-vapor delivery apparatus of claim 9 wherein said fixed-pressure regulator is for regulating pressure at said inlet passageway of said ambient-referenced pressure regulator means to a positive pressure of about 1 p.s.i. (70 cm $H_2O$).

11. The anesthetic-vapor delivery apparatus of claim 10 additionally comprising an oven means for enclosing said positive displacement pump and essentially all of said pump gas-supply conduit and for holding said pump and pump gas-supply conduit to a predetermined fixed oven temperature to prevent condensation of the anesthetic vapor therein.

12. The anesthetic-vapor delivery apparatus of claim 11 wherein said predetermined fixed oven temperature is greater than 25° C.

* * * * *